(12) United States Patent
Panos et al.

(10) Patent No.: US 8,100,895 B2
(45) Date of Patent: Jan. 24, 2012

(54) HEAT TREATING A BIOLOGICAL SITE IN A PATIENT'S BODY

(75) Inventors: James Panos, Kingsford (AU); Jose L. Cincunegui, West Pennant Hills (AU)

(73) Assignee: CathRx Ltd, Homebush Bay, NSW (AU)

( * ) Notice: Subject to any disclaimer, the term of this patent is extended or adjusted under 35 U.S.C. 154(b) by 1044 days.

(21) Appl. No.: 11/983,344

(22) Filed: Nov. 7, 2007

(65) Prior Publication Data

US 2008/0154255 A1 Jun. 26, 2008

Related U.S. Application Data

(60) Provisional application No. 60/872,021, filed on Nov. 29, 2006.

(51) Int. Cl.
*A61B 18/18* (2006.01)
*A61B 18/10* (2006.01)
(52) U.S. Cl. ............ 606/33; 606/32; 606/35; 606/41
(58) Field of Classification Search ............ 606/32–35, 606/41; 607/99, 96, 102
See application file for complete search history.

(56) References Cited

U.S. PATENT DOCUMENTS

| | | |
|---|---|---|
| 5,383,917 A | 1/1995 | Desai et al. |
| 5,810,802 A | 9/1998 | Panescu et al. |
| 6,350,263 B1 | 2/2002 | Wetzig et al. |
| 6,485,487 B1 | 11/2002 | Sherman |
| 2005/0273091 A1 | 12/2005 | Booth et al. |

FOREIGN PATENT DOCUMENTS

| | | |
|---|---|---|
| JP | 2002513620 | 5/2002 |
| JP | 2002238917 | 8/2002 |
| JP | 2006504453 | 2/2006 |

OTHER PUBLICATIONS

Office Action for corresponding Japanese Application No. P2007-0293526, dated Dec. 7, 2010.
"Theory and Lecture of Electrical Devices, vol. 2, (Transformer, Induction machine and AC Commutator type Motor)" published by the Institute of Electrical Engineering of Japan, May 20, 1967, 4 pages, English copy not available.
Partial European Search Report mailed on Apr. 2, 2008 for European Application No. 017254553.6, filed on Nov. 29, 2006, five pages.

*Primary Examiner* — Linda Dvorak
*Assistant Examiner* — Amanda Scott
(74) *Attorney, Agent, or Firm* — TraskBritt

(57) ABSTRACT

A system for heating a site in a patient's body includes a transformer having a primary winding and a secondary winding, the secondary winding having at least one center tap to provide a patient reference and at least two sources of radio frequency (RF) energy, the two sources of RF energy being out of phase with each other. A group of electrodes is connected to the sources of RF energy provided by the secondary winding to be simultaneously energized. The arrangement is such that there are more active electrodes connected to one of the sources of RF energy than another of the sources of RF energy with the energy supplied to one active electrode being out of phase with the energy supplied to an adjacent active electrode.

32 Claims, 1 Drawing Sheet

HEAT TREATING A BIOLOGICAL SITE IN A PATIENT'S BODY

CROSS-REFERENCE TO RELATED APPLICATION

The present application claims priority from U.S. Provisional Application No. 60/872,021, filed on Nov. 29, 2006, the disclosure of which is incorporated herein by reference in its entirety.

FIELD

This invention relates, generally, to the heat treatment of a biological site in a human or animal body. More particularly, the invention relates to a system for, and a method of, heating a biological site in a patient's body to produce at least one lesion at the site or for the treatment of pain management.

BACKGROUND

Electromagnetic energy, in the form of radio frequency (RF) energy, is used to produce lesions at a biological site in the human or animal body for many purposes such as, for example, for cardiac ablation purposes, for tumor ablation, etc. RF energy can also be used for heating a site for the treatment of pain management. To apply the RF energy at the required site in the body, an electrode is used as a conductor with an electrode tip forming a first terminal of the circuit and a back patch beneath the patient's body forming a return electrode for the circuit so that, when the electrode tip is brought into contact with the site, a closed circuit is formed. A problem with this arrangement is that the impedance of the patient's body is high, resulting in dissipation of the RF energy through the patient's body rather than being concentrated at the site.

Traditionally lesions have been produced at a site using a single active electrode system. The RF energy is applied to a small electrode tip toward the end of a catheter with a return path being made via the patient's body.

SUMMARY

According to a first aspect of the invention, there is provided a system for heating a site in a patient's body, the system including a transformer having a primary winding and a secondary winding, the secondary winding having at least one tap to provide a patient reference and at least two sources of radio frequency (RF) energy, the two sources of RF energy being out of phase with each other; and a group of electrodes connected to the sources of RF energy provided by the secondary winding to be simultaneously energized, the arrangement being such that there are more active electrodes connected to one of the sources of RF energy than the other of the sources of RF energy with the energy supplied to one active electrode being out of phase with the energy supplied to an adjacent active electrode.

At least periodically, the group of active electrodes may comprise an odd number of electrodes with a sub-group of an even number of active electrodes being connected to one of the sources of RF energy and a sub-group of an odd number of active electrodes being connected to the other of the sources of RF energy and the active electrodes of the sub-groups alternating with one another along a length of a catheter carrying the electrodes. More particularly, the group of electrodes may comprise at least three active electrodes that are energized simultaneously with the energy supplied to one sub-group comprising two outer electrodes of the group of three active electrodes being in phase with each other but out of phase with the energy supplied to another sub-group comprising a single, inner, or middle, active electrode arranged between the two outer electrodes of the one sub-group.

The system may include a switching arrangement interposed between the secondary winding of the transformer and the group of electrodes periodically to change the configuration of active electrodes connected to the sources of RF energy.

It will be appreciated that it is not necessary and that it is always the same active electrode that is connected to the one sub-winding. In practice, this may not in fact be the case. For example, in a three electrode system, electrode 1 may initially be connected to the first sub-winding and electrode 3 may be connected to the second sub-winding. After a predetermined period of time, electrodes 1 and 3 may be connected together to the first sub-winding under the action of the switching arrangement and electrode 2 may be connected to the second sub-winding.

The system may include a monitoring device associated with each electrode for monitoring the energy supplied to each active electrode. The monitoring device may be a temperature sensing device, such as a thermocouple or thermistor, for monitoring the temperature of its associated active electrode. In addition, monitoring devices may also be arranged between adjacent electrodes. The monitoring devices may be connected to the switching arrangement, the switching arrangement being responsive to a monitored parameter of each active electrode for feedback control of the magnitude of RF energy to be supplied to the active electrodes and/or for switching between configurations of electrodes connected to the sources of RF energy. For example, the switching arrangement may select the appropriate thermocouple, i.e., the thermocouple associated with the hottest active electrode, in order to control the magnitude of the RF energy to be delivered to the electrodes. Other monitoring devices may include pressure sensors, fiber-optic devices, impedance measuring devices, or the like.

The system may include an energy generator for generating the RF energy, the primary winding of the transformer being connected to an output of the energy generator. The generator may be responsive to the switching arrangement and to the monitored parameter of the active electrodes, as monitored by the monitoring devices, to control the RF energy supplied to the active electrodes.

The transformer may have a 1:1 ratio between the primary winding and the secondary winding. The tap may be a center tap to provide two sub-windings that act as energy sources with the energy supplied by the sources being 180° out of phase, with respect to each other.

In an embodiment, at least one of the electrodes connected to each source of RF energy may not be active at the time that at least one other electrode connected to that source of RF energy is active.

According to a second aspect of the invention, there is provided a system for heating a site in a patient's body, the system including a transformer having a primary winding and a secondary winding, the secondary winding having at least one tap to provide a patient reference and at least two sources of radio frequency (RF) energy, the two sources of RF energy being out of phase with each other; and a plurality of active electrodes connected to the sources of RF energy provided by the secondary winding to be simultaneously energized, with multiple active electrodes being connected to one of the sources of RF energy and a different number of active electrodes being connected to the other source of RF energy and the energy supplied to each of the multiple active electrodes being of the same phase but out of phase, with the energy supplied to each of the different number of active electrodes.

The amplitude of the energy supplied to each of the multiple active electrodes may be less than the amplitude of the energy supplied to each of the different number of active electrodes.

The system may include an energy generator for generating the RF energy, with the primary winding of the transformer being connected to an output of the energy generator. The generator may be responsive to the switching arrangement and to a monitored parameter of the electrodes, as monitored by a monitoring device associated with each electrode, to control the RF energy supplied to the electrodes. The monitored parameter of each electrode may be a temperature of each electrode. Thus, the monitoring device associated with each electrode may be a temperature sensing device, such as a thermocouple or thermistor.

The transformer may have a 1:1 ratio between the primary winding and the secondary winding. The tap may be a center tap to provide two sub-windings that act as energy sources with the energy supplied by the sources being 180° out of phase, with respect to each other.

At least one active electrode may be connected to one sub-winding and at least two active electrodes may be connected to the other sub-winding.

According to a third aspect of the invention, there is provided a method of heating a site in a patient's body, the method including providing a transformer having a primary winding and a secondary winding, the secondary winding having at least one tap to provide a patient reference and at least two sources of radio frequency (RF) energy, the at least two sources of RF energy being out of phase with each other; and connecting a group of electrodes to the sources of RF energy provided by the secondary winding to be simultaneously energized, the arrangement being such that there are more active electrodes connected to one of the sources of RF energy than the other of the sources of RF energy with the energy supplied to one active electrode being out of phase with the energy supplied to an adjacent active electrode.

The method may include, at least periodically, selecting an odd number of active electrodes to constitute the group of electrodes, connecting a sub-group comprising an even number of active electrodes to one of the sources of RF energy and a sub-group comprising an odd number of active electrodes to the other of the sources of RF energy, with the active electrodes of the sub-groups alternating with one another along a length of a catheter carrying the electrodes. More particularly, the method may include selecting the group of electrodes to comprise at least three active electrodes, which are energized simultaneously with the energy supplied to a sub-group comprising two outer active electrodes of the group of three electrodes being in phase with each other but out of phase with the energy supplied to a sub-group comprising a single, inner active electrode arranged between the two outer electrodes of the one sub-group.

The method may include interposing a switching arrangement between the secondary winding of the transformer and the group of electrodes periodically to change the configuration of electrodes connected to the sources of RF energy.

Further, the method may include monitoring the energy supplied to each active electrode. The method may include monitoring and controlling the energy supplied to each active electrode by monitoring the temperature of each electrode and selecting the hottest electrode for feedback control.

The method may include connecting at least one active electrode to one sub-winding and connecting at least two active electrodes periodically to the other sub-winding.

The method may include, periodically, having the same number of electrodes connected to each source of RF energy.

In an embodiment, the method may include deactivating at least one of the electrodes connected to each source of RF energy at the time that at least one other electrode connected to that source of RF energy is active.

The method may include activating a sub-group of electrodes of the group of the electrodes while the remaining electrodes of the group of electrodes are deactivated and, after a period of time, activating a different sub-group of electrodes. Preferably, the method includes selecting the same number of electrodes to constitute each activated sub-group of electrodes.

According to a fourth aspect of the invention, there is provided a method of heating a site in a patient's body, the method including providing a transformer having a primary winding and a secondary winding, the secondary winding having at least one tap to provide a patient reference and at least two sources of radio frequency (RF) energy, the two sources of RF energy being out of phase with each other; and connecting a plurality of electrodes to the sources of RF energy provided by the secondary winding to be simultaneously energized, with multiple active electrodes being connected to one of the sources of RF energy and a different number of active electrodes being connected to the other source of RF energy and the energy supplied to each of the multiple active electrodes being of the same phase, but out of phase with the energy supplied to each of the different number of active electrodes.

The method may include supplying energy to each of the multiple active electrodes which has an amplitude less than the amplitude of the power supplied to each of the different number of active electrodes.

The method may include connecting at least one active electrode to one sub-winding and connecting at least two active electrodes to the other sub-winding.

DETAILED DESCRIPTION OF EXEMPLARY EMBODIMENTS

Figure 1:
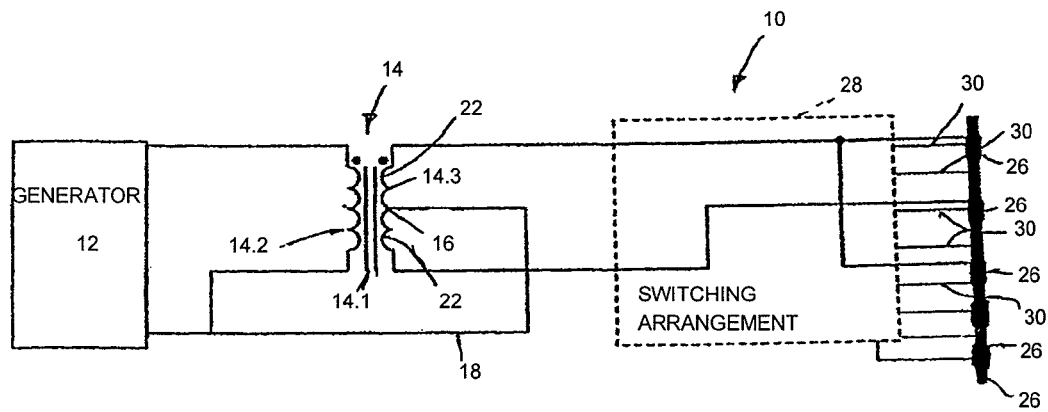
FIG. 1 shows a schematic block diagram of an embodiment of a system for heating a biological site in a patient's body, the system being shown in a first configuration.

In the drawings, reference numeral 10 generally designates a system, in accordance with an embodiment of the invention, for heating a site in patient's body. The system 10 includes a generator 12 for generating electromagnetic energy, more particularly, radio frequency (RF) energy.

The generator 12 is in communication with a transformer 14. The transformer 14 has a core 14.1, a primary winding 14.2 and a secondary winding 14.3. The secondary winding 14.3 of the transformer 14 is a center tapped transformer having a center tap 16. The center tap 16 is connected via a return line 18 to the generator 12.

The center tap 16 creates two sub-windings 22, to each of which at least one active electrode 24 of a catheter 26 is connectable. By "active" it is meant that, unless the context clearly indicates otherwise, the electrode is used to impart energy to the site.

The arrangement of the sub-windings 22 is such that, due to the center tap 16, energy supplied by one sub-winding 22 is 180° out of phase with the energy supplied by the other sub-winding 22.

The transformer 14 makes use of a 1:1 ratio between the primary winding 14.2 and the secondary winding 14.3. In addition, the materials used in the transformer 14 are selected to be capable of withstanding energy levels and frequencies involved in ablative therapies. The transformer 14 and the materials used are optimized to ensure maximum transfer of energy from the transformer 14 to the active electrodes 24.

Suitable materials for the transformer include nickel-zinc or manganese-zinc ferrites for the core 14.1 of the transformer 14, in particular F8, F12 and F14 ferrites. These materials are able to operate at the required frequencies and have the necessary high initial permeability and high saturation flux. The dimension of the core 14.1, the number of turns of the windings 14.2 and 14.3 and the diameter of the windings 14.2 and 14.3 are selected so that the transformer 14 has low insertion losses to ensure efficient transfer of energy.

The primary winding 14.2 of the transformer 14 is matched to the output impedance of the generator 12. The generator 12 has an output impedance of between about 30 ohms and 300 ohms. If necessary, a series resistor and/or a parallel capacitor can be included to effect impedance matching.

The active electrodes 24 are connected to the secondary winding 14.3 of the transformer 14 via a switching arrangement 28, as shown by dashed lines. In addition, each active electrode 24 has a thermocouple, illustrated schematically by each line 30, connected to the switching arrangement 28 for the control of energy to the active electrodes 24 by the system 10. The system 10 also includes a thermocouple 30 connected between adjacent electrodes 24 for more accurate temperature control.

The system 10 is intended for use in the production of lesions at a site in a patient's body for treating various disorders such as atrial fibrillation, ventricular tachycardia, tumor ablation, or the like, or for heat treating the site in the treatment of pain management. In the case of pain management, it may not be necessary that lesions are actually created, rather that heat treating of the site effects management of the pain.

In the case of atrial fibrillation, abnormal electrical impulse activity in the tissue gives rise to irregular heart rhythms. This necessitates the formation of a large number of spot lesions. This is a time consuming and difficult process and may result in excessive charring of the tissue. It is also necessary that the spots overlap to ensure that the undesirable signal path is interrupted. Thus, accurate placement of the ablating electrode of a catheter is required. Also, use is made of a back plate as a return electrode thereby resulting in excessive dissipation of energy through the patient's body.

If it were possible to form longer lesions, the number of lesions to be formed can be reduced thereby improving the accuracy of the technique and minimizing damage to the tissue.

In use, in an initial configuration, the electrodes 24 are connected to the secondary winding 14.3 of the transformer 14 in the configuration shown in FIG. 1 of the drawings. Thus, a sub-group comprising two outer electrodes 24 of a group of three electrodes 24 is connected to one of the sub-windings 22 with a sub-group comprising the inner electrode 24 of the group of three electrodes 24 being connected to the other sub-winding 22. The energy supplied to each outer electrode 24 is half that of the energy supplied to the inner electrode 24. In addition, the energy supplied to the outer electrodes 24, while being in phase with each other, is out of phase with the energy supplied by the sub-winding 22 to the inner electrode 24. More particularly, the energy supplied to the outer electrodes 24 is 180° out of phase with the energy supplied to the inner electrode 24.

While this embodiment has been described with reference to the use of three active electrodes 24, it will be appreciated that any desired number of electrodes could be used. For example, a five active electrode system would have electrodes 1, 3 and 5 connected to one of the sub-windings 22 with a phase angle of the energy of 0° with electrodes 2 and 4 being connected to the other sub-winding 22 with a phase angle of the energy of 180°.

Using this arrangement of energizing alternate electrodes of a group of electrodes, a longer, more confluent lesion is formed that concentrates the ablation to extend between inner ends of the outer electrodes 24 of the group of electrodes. The connection of electrodes 1 and 3 to the same phase is done using the switching arrangement 28 and may incorporate a relay or a mechanical switch.

In a variation of this embodiment, the switching arrangement 28 includes a timing mechanism. Initially, energy is supplied to the site using the three active electrodes 24 (in this example) in the configuration shown in FIG. 1 of the drawings. After a predetermined period of time, the switching of the electrodes changes so that electrode 1 is connected to one of the sub-windings 22 and electrode 3 is connected to the other sub-winding 22, with electrode 2 not being connected to either sub-winding 22. With this arrangement, an even longer, confluent lesion is formed that extends over the entire length of the distance covered by the three electrodes. In other words, a lesion is formed up to the outer ends of the outer electrodes 24 with a very rectangular appearance and a more uniform depth than with a traditional, single electrode system.

The system 10 could also have a number of inactive electrodes connected to each sub-winding of the transformer 14. Thus, in another embodiment, a cascading-like effect can be imparted to a series of electrodes 24 for creating a longer lesion but with lower power consumption. Thus, for example, if one sub-winding 22 had three electrodes 24 connected to it and the other sub-winding 22 had two electrodes connected to it, the switching arrangement 28 could be configured to energize only three electrodes 24 at any one time. In this embodiment, one active electrodes 24 of one sub-winding 22 is interposed between two active electrodes both connected to the other sub-winding 22 so that the energy supplied to the middle active electrode 24 is 180° out of phase with the energy supplied to the two outer electrodes 24. The remaining electrodes 24 connected to the sub-windings 22 are not energized and are inactive.

Thus, electrodes 1 and 3 connected to the first sub-winding 22 and electrode 2 connected to the second sub-winding 22 are energized initially and are active with electrodes 4 and 5 being de-energized and inactive. After a period of time, for example, five seconds, there is a "shift" of active electrodes. More particularly, electrode 1 is de-energized to become inactive, electrodes 2 and 4 are active and are connected to one sub-winding 22, electrode 3 is active and is connected to the other sub-winding 22 and electrode 5 remains de-energized. After yet a further period of time, for example, a further five seconds, there is a further "shift" of active electrodes. Thus, electrodes 1 and 2 are rendered inactive, electrodes 3 and 5 are active and are connected to the one sub-winding 22 and electrode 4 is active and is connected to the other sub-winding 22.

In this way, a longer lesion can be formed with reduced power consumption. For example, instead of 50 W to activate five electrodes simultaneously, only 30 W is required to energize three electrodes at a time. While the procedure may take a little longer to perform, better depth control can be effected to create an improved lesion.

It will also be appreciated that the cascading effect need not move along by one electrode at a time. Two or more electrodes in the series can be activated and deactivated at a time. In addition, the cascading effect need not move in one direction only; switching of the cascading effect back and forth can be effected by the switching arrangement 28 to control lesion formation.

Figure 2:
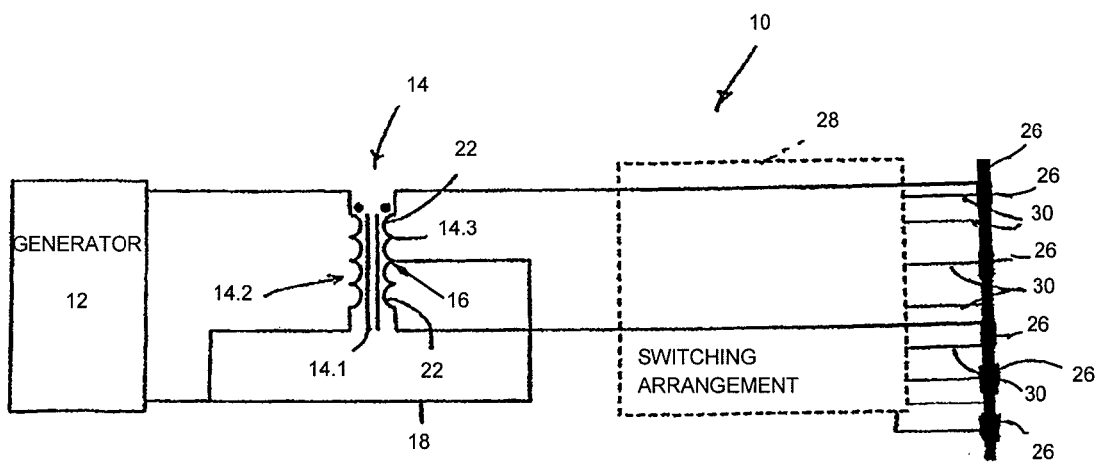
FIG. 2 shows a schematic block diagram of the system in a second configuration.

The switching arrangement 28 is configured to switch only once in an ablating period between the two configurations as shown in FIGS. 1 and 2 of the drawings. Instead, the switching arrangement 28 can be configured to switch periodically between the two configurations during an ablating period. The latter switching technique may be beneficial in enabling more accurate temperature control during the lesion formation.

The switching arrangement 28 monitors the temperature of all the thermocouples 30 of the system 10 in real time. To coincide with each intermittent ablation configuration, the thermocouple 30 selected for control of RF energy is selected based on the location of most energy activity, i.e., the thermocouple reading associated with the hottest electrode 24. The temperature of the hottest electrode 24 is fed back to the generator 12 by the switching arrangement 28. The generator 12 then controls the energy delivered to all the electrodes 24 based on the temperature data received from the switching arrangement 28.

The center tap 16 functions as a reference patch and the connection 18 functions as a return path of the system 10. The reference patch and the connection 18 of the system 10 are used only in the event that the connection of the electrode(s) 24 to one of the sub-windings 22 is lost. Apart from that, energy transfer takes place between adjacent electrodes 24 of the system 10 resulting in a more efficient use of the energy during an ablation or heat treatment process.

While the system 10 has been described with reference to a single electrode 24 constituting each electrode of a group connected to the secondary winding 14.3 of the transformer 14, it will be appreciated that each electrode 24 could comprise a number of sub-electrodes making up the electrode 24. A further variation of the arrangement of these sub-electrodes could be to alternate the RF energy delivered to the sub-electrodes with respect to each other to assist in lesion formation.

It is an advantage of the invention that, because lower power is supplied to each electrode 24 than with a single ablating electrode system, there is less charring of the tissue.

As described above, longer, more confluent and uniform lesions are formed than using a single ablating electrode. This improves the likelihood of interrupting signal paths in the tissue giving rise to the cardiac abnormalities or other abnormalities being treated.

Because lesion formation occurs between two electrodes, the inter-electrode impedance much lower than that through a patient's body resulting in improved energy transfer between the electrodes 24 rather than dissipation of energy through the patient's body. By avoiding such large dissipation of energy through the patient's body, it also reduces the risk of surface tissue burns to the patient in the event of a poor tissue-electrode interface at the patient reference patch location.

It is still another advantage of the invention that the use of at least three electrodes is of benefit in creating more uniform, confluent, linear lesions such as are used in "Maze"-like procedures.

The system 10 is easy to implement due to the use of a center tapped transformer rather than the need for any dedicated phase-shifting systems or mechanisms.

It will be appreciated by a person skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A system for heating a site in a patient's body, the system including:
a transformer having a primary winding and a secondary winding, the secondary winding having at least one tap to provide a patient reference and at least two sources of radio frequency (RF) energy, the at least two sources of RF energy being out of phase with each other; and
a group of electrodes connected to the at least two sources of RF energy provided by the secondary winding to be simultaneously energized, the arrangement being such that there are more active electrodes connected to one of the at least two sources of RF energy than another of the sources of RF energy with the energy supplied to one active electrode being out of phase with the energy supplied to an adjacent active electrode.

2. The system of claim 1, wherein at least periodically, the group of electrodes comprises an odd number of active electrodes with a sub-group of an even number of active electrodes being connected to one of the sources of RF energy and a sub-group of an odd number of active electrodes being connected to the another of the sources of RF energy and the active electrodes of the sub-groups alternating with one another along a length of a catheter carrying the electrodes.

3. The system of claim 2, wherein the group of electrodes comprises at least three active electrodes which are energized simultaneously with the energy supplied to one sub-group comprising two outer active electrodes of the group of three electrodes being in phase with each other but out of phase with the energy supplied to a sub-group comprising a single, inner active electrode arranged between the two outer electrodes of one group.

4. The system of claim 1, further including a switching arrangement interposed between the secondary winding of the transformer and the group of electrodes periodically to change a configuration of electrodes connected to the sources of RF energy.

5. The system of claim 4, further including a monitoring device associated with each electrode for monitoring the energy supplied to each active electrode.

6. The system of claim 5, wherein the monitoring device is a temperature sensing device for monitoring the temperature of its associated active electrode.

7. The system of claim 5, wherein the monitoring device is connected to the switching arrangement, the switching arrangement being responsive to a parameter of each active electrode, monitored by its associated monitoring device, for feedback control of the magnitude of RF energy to be supplied to the electrodes and/or for switching between configurations of electrodes connected to the sources of RF energy.

8. The system of claim 4, further including an energy generator for generating the RF energy, the primary winding of the transformer being connected to an output of the energy generator.

9. The system of claim 8, wherein the generator is responsive to the switching arrangement and to the monitored parameter of the active electrodes, as monitored by the monitoring devices, to control the RF energy supplied to the active electrodes.

10. The system of claim 1, wherein the transformer has a 1:1 ratio between the primary winding and the secondary winding.

11. The system of claim 1, wherein the tap is a center tap to provide two sub-windings that act as energy sources with the energy supplied by the two sub-windings being 180° out of phase with respect to each other.

12. The system of claim 1, wherein at least one of the electrodes connected to each source of RF energy is not active at the time that at least one other electrode connected to that source of RF energy is active.

13. A system for heating a site in a patient's body, the system including:
a transformer having a primary winding and a secondary winding, the secondary winding having at least one tap to provide a patient reference and at least two sources of radio frequency (RF) energy, the at least two sources of RF energy being out of phase with each other; and
a plurality of electrodes connected to the at least two sources of RF energy provided by the secondary winding to be simultaneously energized, with multiple active electrodes being connected to one of the sources of RF energy and a different number of active electrodes connected to another source of RF energy and the energy supplied to each of the multiple active electrodes being of the same phase but out of phase with the energy supplied to each of the different number of active electrodes.

14. The system of claim 13, wherein an the amplitude of the energy supplied to each of the multiple active electrodes is less than an amplitude of the energy supplied to each of the different number of active electrodes.

15. The system of claim 13, further including an energy generator for generating the RF energy, the primary winding of the transformer being connected to an output of the energy generator.

16. The system of claim 15, wherein the generator is responsive to a switching arrangement and to a monitored parameter of the electrodes, as monitored by a monitoring device associated with each electrode, to control the RF energy supplied to the multiple active electrodes.

17. The system of claim 13, wherein the transformer has a 1:1 ratio between the primary winding and the secondary winding.

18. The system of claim 13, wherein the tap is a center tap to provide two sub-windings that act as energy sources with the energy supplied by the two sub-winding being 180° out of phase with respect to each other.

19. The system of claim 18, wherein at least one active electrode is connected to one sub-winding and at least two active electrodes are connected to another sub-winding.

20. A method of heating a site in a patient's body, the method including:
providing a transformer having a primary winding and a secondary winding, the secondary winding having at least one tap to provide a patient reference and at least two sources of radio frequency (RF) energy, the at least two sources of RF energy being out of phase with each other; and
connecting a group of electrodes to the at least two sources of RF energy provided by the secondary winding to be simultaneously energized, the arrangement being such that there are more active electrodes connected to one of the at least two sources of RF energy than another of the at least two sources of RF energy with the energy supplied to one active electrode being out of phase with the energy supplied to an adjacent active electrode.

21. The method of claim 20, further including at least periodically, selecting an odd number of electrodes to constitute the group of electrodes, connecting a sub-group comprising an even number of active electrodes to one of the sources of RF energy and a sub-group comprising an odd number of active electrodes to another of the sources of RF energy, with the active electrodes of the sub-groups alternating with one another along a length of a catheter carrying the electrodes.

22. The method of claim 21, further including selecting the group of electrodes to comprise at least three active electrodes which are energized simultaneously with the energy supplied to one sub-group comprising two outer active electrodes of the group of three electrodes being in phase with each other but out of phase with the energy supplied to another sub-group comprising a single, inner active electrode arranged between the two outer electrodes of the one sub-group.

23. The method of claim 22, further including interposing a switching arrangement between the secondary winding of the transformer and the group of electrodes periodically to change a configuration of electrodes connected to the at least two sources of RF energy.

24. The method of claim 22, further including monitoring the energy supplied to each active electrode.

25. The method of claim 24, further including monitoring and controlling the energy supplied to each active electrode by monitoring a temperature of each active electrode and selecting the hottest electrode for feedback control.

26. The method of claim 20, further including connecting at least one active electrode to one sub-winding and connecting at least two active electrodes periodically to another sub-winding.

27. The method of claim 20, further including deactivating at least one of the electrodes connected to each source of RF energy at the time that at least one other electrode connected to that source of RF energy is active.

28. The method of claim 27, further including activating a sub-group of electrodes of the group of the electrodes while the remaining electrodes of the group of electrodes are deactivated and, after a period of time, activating a different sub-group of electrodes.

29. The method of claim 28, further including selecting the same number of electrodes to constitute each activated sub-group of electrodes.

30. A method of heating a site in a patient's body, the method including
providing a transformer having a primary winding and a secondary winding, the secondary winding having at least one tap to provide a patient reference and at least two sources of radio frequency (RF) energy, the at least two sources of RF energy being out of phase with each other; and
connecting a plurality of electrodes to the at least two sources of RF energy provided by the secondary winding to be simultaneously energized, with multiple active electrodes being connected to one of the sources of RF energy and a different number of active electrodes being connected to another source of RF energy and the energy supplied to each of the multiple active electrodes being of the same phase but out of phase with the energy supplied to each of the different number of active electrodes.

31. The method of claim 30, further including supplying energy to each of the multiple active electrodes that has an amplitude less than the amplitude of the power supplied to each of the different number of active electrodes.

32. The method of claim 30, further including connecting at least one active electrode to one sub-winding and connecting at least two active electrodes to another sub-winding.

* * * * *

UNITED STATES PATENT AND TRADEMARK OFFICE
CERTIFICATE OF CORRECTION

PATENT NO. : 8,100,895 B2
APPLICATION NO. : 11/983344
DATED : January 24, 2012
INVENTOR(S) : James Panos and Jose L. Cincunegui It is certified that error appears in the above-identified patent and that said Letters Patent is hereby corrected as shown below:

In the specification:
COLUMN 3, LINE 2, change "same phase but out of phase," to --same phase, but out of phase--

In the claims:
CLAIM 14, COLUMN 9, LINE 34, change "wherein an the" to --wherein an--

Signed and Sealed this
Twentieth Day of October, 2015

Michelle K. Lee
*Director of the United States Patent and Trademark Office*